(12) United States Patent
Kaneda

(10) Patent No.: US 8,722,355 B2
(45) Date of Patent: May 13, 2014

(54) MEASUREMENT METHOD USING OXIDASE

(75) Inventor: Hisashi Kaneda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 12 days.

(21) Appl. No.: 13/277,473

(22) Filed: Oct. 20, 2011

(65) Prior Publication Data

US 2012/0100567 A1 Apr. 26, 2012

(30) Foreign Application Priority Data

Oct. 22, 2010 (JP) ................................. 2010-237379

(51) Int. Cl.
*C12Q 1/26* (2006.01)
(52) U.S. Cl.
USPC .......................................................... 435/25
(58) Field of Classification Search
None
See application file for complete search history.

(56) References Cited

U.S. PATENT DOCUMENTS

| | | | |
|---|---|---|---|
| 6,212,417 B1 | 4/2001 | Ikeda et al. | ................... 600/345 |
| 2005/0247573 A1 | 11/2005 | Nakamura et al. | |
| 2007/0131549 A1 | 6/2007 | Cai et al. | ................. 204/403.02 |

FOREIGN PATENT DOCUMENTS

| | | | |
|---|---|---|---|
| EP | 1734362 A2 | 12/2006 | |
| JP | 10-282038 | 10/1998 | ........... G01N 27/327 |
| JP | 2000-65778 | 3/2000 | ........... G01N 27/327 |
| JP | 2007-163499 | 6/2007 | ............ G01N 27/27 |
| JP | 2010-054379 A | 3/2010 | |

OTHER PUBLICATIONS

Kurahashi et al., "Influence of blood sample oxygen tension on blood glucose concentration measured using an enzyme-electrode method," Critical Care Medicine, 25: 231-235 (1997).
Extended Search Report issued in corresponding European Patent Application No. 11186208.2 dated May 31, 2013.
Office Action issued in corresponding Japanese Patent Application No. 2011-229546 dated Mar. 11, 2014.

*Primary Examiner* — Suzanne M Noakes
(74) *Attorney, Agent, or Firm* — Morgan, Lewis & Bockius LLP

(57) ABSTRACT

A method for measuring a target object in a sample by using an oxidase, wherein the influence of dissolved oxygen in the sample can be corrected, is provided. The method comprises: obtaining measurement values by causing the target object in the sample to react with the oxidase under different conditions of two or more types; and performing a correction based on the obtained two or more measurement values and a correction method preliminarily set so as to correct the influence of dissolved oxygen in the sample.

13 Claims, 3 Drawing Sheets

MEASUREMENT METHOD USING OXIDASE

CROSS-REFERENCE TO RELATED APPLICATION

This application claims priority to JP 2010-237379, filed Oct. 22, 2010 which is hereby incorporated by reference in its entirety.

TECHNICAL FIELD

The present invention relates to a measurement method using an oxidase, and to a biosensor and a measurement device used in the measurement method.

BACKGROUND ART

Practical application of enzyme sensors has been advanced particularly, as compared with other biosensors. For example, enzyme sensors for measuring glucose, lactic acid, cholesterol, lactose, uric acid, urea, and amino acids are used in medical measurement and in the food industry. An enzyme sensor performs a quantitative analysis of an analyte by reducing an electron acceptor (mediator) with electrons generated by reaction between an enzyme and a target object to be measured (substrate) contained in a sample solution that is a liquid, and electrochemically measuring an oxidation-reduction degree of the electron acceptor. In the case where blood is the sample solution, however, there is the problem that an accurate assay cannot be performed by a biosensor using an oxidation-reduction enzyme, due to the influence of dissolved oxygen. Particularly, an enzyme sensor utilizing GOD (glucose oxidase) is often used in measurement upon a pre-meal insulin injection and evaluation of hypoglycemia. If a higher concentration of glucose than the actual level is indicated due to the influence of dissolved oxygen, this could lead to excessive administration of insulin, and the hypoglycemia would remain undetected. Therefore, a biosensor is in demand that is not influenced by dissolved oxygen even if it is used with respect to a sample that could possibly contain dissolved oxygen, such as blood.

As a technique for avoiding the influence of dissolved oxygen, a method using a third electrode (JP 10(1998)-282038 A, JP 2000-065778 A), and an enzyme sensor using GDH (glucose dehydrogenase) (JP 2007-163499 A), etc. have been developed. On the other hand, it has been pointed out that new capital investment is needed in the case of the method using a third electrode, and that as to the method using GDH, enzyme costs of GDH are higher than that of GOD, and the method is likely to be influenced by saccharides such as maltose that hinder the measurement.

SUMMARY OF THE INVENTION

Problem to be Solved by the Invention

To cope with these problems, a measurement method using an oxidation-reduction enzyme biosensor, with which capital investment can be reduced and enzyme costs can be decreased, has been desired. The present invention provides a method for measuring a target object in a sample using an oxidase, wherein the influence by dissolved oxygen in the sample can be corrected.

Means to Solve the Problem

The present invention relates to a method for measuring a target object in a sample, the method including: obtaining measurement values by reacting a target object in a sample with an oxidase under different conditions of two or more types; and performing a correction based on the obtained two or more measurement values and a correction method preliminarily set so as to correct influences of dissolved oxygen in the sample.

The present invention in another aspect relates to a biosensor including: two or more independent electrode systems each of which comprises a working electrode and a counter electrode provided on a substrate; and oxidase-containing reagents provided respectively on the two or more electrode systems, the oxidase-containing reagents being capable of measuring a single target object in a single sample under different conditions. Further, the present invention in still another aspect relates to a measurement device for measuring a target object, the measurement device including: a sensor section for obtaining information about measurement results obtained from reactions between a target object in a sample and an oxidase under different conditions of two or more types; a memory section for storing a correction method; an arithmetic section for selecting the correction method stored in the memory section based on the information obtained by the sensor section, and calculating a corrected value of the information by the correction method; and a display section for displaying the corrected value.

Effects of the Invention

With the measurement method of the present invention, even in the presence of dissolved oxygen, a concentration of a target object can be determined with the influence of dissolved oxygen being corrected with use of an oxidase. Further, the present invention preferably makes it possible to correct the influence of dissolved oxygen without using an enzyme other than an oxidase, for example, GDH. Further, the present invention preferably makes it possible to correct the influence of dissolved oxygen without using a third electrode.

DETAILED DESCRIPTION OF THE INVENTION

Figure 1:
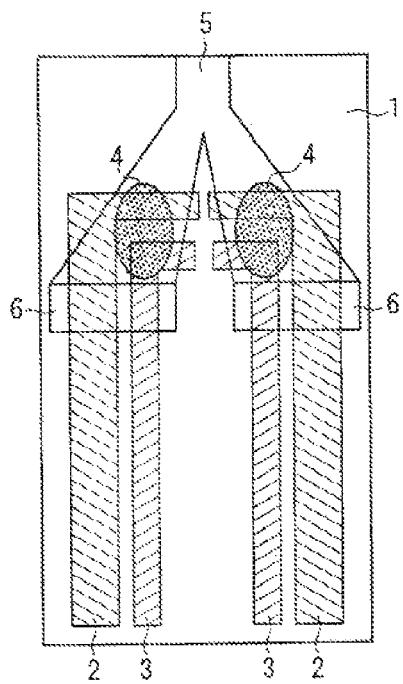
FIG. 1 is a schematic diagram illustrating a configuration of an embodiment of a biosensor according to the present invention.

The present invention is based on knowledge that, in measurements using oxidase electrode systems, corrections based on results in two types of reaction systems that differ from each other in reaction conditions (for example, the oxygen amount, the type of mediator, etc.) can reduce the influence of dissolved oxygen.

More specifically, the present invention relates to a method for measuring a target object in a sample using an oxidase, the measurement method including: obtaining measurement values by causing the target object in the sample to react with the oxidase under different conditions of two or more types; and performing a correction based on the obtained two or more measurement values and a correction method preliminarily set so as to correct the influence of dissolved oxygen in the sample (hereinafter this method is also referred to as "the measurement method of the present invention"). The measurement method of the present invention enables measurement in which influences of dissolved oxygen in a sample can be corrected.

The mechanism of predicting an amount of dissolved oxygen based on measurement values obtained by measurement under different conditions of two or more types is considered to be as follows. When an oxidase enzyme is used, the concentration of dissolved oxygen influences the oxygen-mediator reaction (see the scheme shown below). It is presumed that variation of a magnitude of this influence depending on differences in the reaction conditions makes an output time course different. However, the interpretation of the present invention may not be limited to the interpretation based on this mechanism.

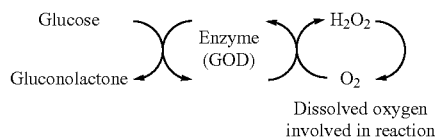

In the present specification, "target object" refers to an object that is to be measured by the method of the present invention and that becomes a substrate of an oxidase. Examples of the same include, but are not limited to, glucose, lactic acid, bilirubin, cholesterol, and ascorbic acid. Therefore, as to the oxidase that is to react with a target object, any oxidase having the target object as a substrate thereof can be used in the present invention. Examples of such an oxidase include, but are not limited to, glucose oxidase, lactate oxidase, bilirubin oxidase, cholesterol oxidase, and ascorbic acid oxidase. Further, examples of the oxidase that can be used in the measurement method of the present invention include, but are not limited to, uric acid oxidase, peroxidase, sulfurous acid oxidase, amine oxidase, lysyl oxidase, lysine oxidase, amino acid oxidase, diamine oxidase, pyridoxine phosphate oxidase, protein-lysine 6-oxidase, acyl-CoA oxidase, alcohol oxidase, choline oxidase, pyruvic acid oxidase, sarcosine oxidase, tyramine oxidase, and glycerophosphate oxidase. Substrates of these may be target objects.

In the present specification, the "sample" refers to, unless otherwise provided particularly, a composition or a mixture used in the measurement method of the present invention in which a target object exists or can possibly exist. Examples of the sample include liquid containing a target object or liquid that can generate a target object, for example, biological samples such as blood, plasma, serum, urine, and body fluid.

In the present specification, "causing a target object in a sample to react with an oxidase" refers to bringing a sample into contact with an oxidase so as to cause a target object to react with the oxidase. A reagent containing an oxidase may be of a dry type or of a wet type, but from the viewpoint of simplification, a sample and an oxidase are preferably brought into contact with each other on a biosensor. "Measurement values" are, for example, electric current values in the case where electrode systems are used, or absorbances or transmittances in the case where optical detection is performed, but they are not particularly limited as long as they are measurement values obtained by detection about reaction between a target object and an oxidase. From the viewpoint of simplification, "causing a target object in a sample to react with an oxidase" is preferably performed in a biosensor provided with electrode systems. In the case where electrode systems are used, a mediator is preferably contained in a reaction system.

In the present specification, "different conditions of two or more types" refers to different conditions of at least two types under which a reaction is caused to occur, the conditions of at least two types being different regarding at least one of conditions of reaction between a target object and an oxidase, so that measurement values of at least two types are obtained. The different reaction conditions are not particularly limited, but examples of the same include a type and/or amount of an oxidase, a reaction temperature, a reaction time, a type and/or amount of a mediator, a type and/or amount of a hydrophilic polymer, a type and/or amount of a surfactant, and a type and/or amount of a saccharide.

In the specification, examples of the "measurement value" include results detected about reaction between a target object and an oxidase, and more specifically include electric current values, resistance values, absorbances, transmittances, and values obtained from these (for example, concentrations calculated with use of finite differences, areas, and calibration curves).

[Correction Method]

A correction method can be set preliminarily by preliminarily obtaining measurement values from a plurality of samples having different dissolved oxygen concentrations under predetermined reaction conditions of two or more types. The following can be suggested, for example: a quotient or a difference of respective measurement values A and B of different reaction systems A and B is related with a concentration of dissolved oxygen, and a correction method is set based on it. It should be noted that in the present specification, a measurement value corrected by the measurement method of the present invention is referred to as "corrected value".

One embodiment of the correction method is, for example, correction using a quotient of measurement values A and B (B/A or AB) that are obtained from reaction systems A and B, respectively. One example is a method of obtaining a corrected concentration by multiplying a concentration A obtained from a measurement value A with a quotient B/A of measurement values. It should be noted that regarding the obtainment of a concentration A from a measurement value A, it may be, as conventionally, performed by using calibration curves, etc. This correction method is based on the following knowledge: that influences by dissolved oxygen on an oxidase reaction system depend on an amount of a reagent such as an oxidase in the reaction system; and that in reaction systems A and B that are different in reaction conditions of a reagent containing an oxidase, correction can be achieved by multiplication with a quotient (B/A or AB) of measurement values A and B. It should be noted that in the present embodiment, from the viewpoint of improving correction accuracy further, multiplication with a correction coefficient c in addition to the quotient of measurement values is preferred. This constant depends on predetermined reaction conditions, and it can be set easily by preliminarily performing experiments under the predetermined reaction conditions. Therefore, a preferable style of correction in the present embodiment is correction of multiplying a concentration A obtained from a measurement value A with a quotient B/A of measurement values and a correction coefficient c. The constant c may be 1.

Another embodiment of the correction method suggested herein is, for example, as follows: a concentration (or range thereof) of dissolved oxygen is related with a quotient or a difference of measurement values A and B based on preliminarily obtained date, and execution/non-execution of correction and contents of the correction (e.g., an amount of correction, a correction coefficient, etc.) corresponding to the concentration or range of dissolved oxygen are set.

[Biosensor]

In the measurement method of the present invention, reaction between a target object and an oxidase may be performed in a biosensor including electrode systems each of which has a working electrode and a counter electrode, and reagent layers containing an oxidase, the layers being provided on the electrode systems. It should be noted that the reagent layer contains a mediator generally.

Examples of the mediator usable in the biosensor include, but are not limited to, potassium ferricyanide, sodium ferricyanide, p-benzoquinone and derivatives of the same, phenazine methosulfate and derivatives of the same, indophenol and derivatives of the same, potassium β-naphthoquinone-4-sulfonate, 2,6-dichlorophenol indophenol, methylene blue, nitrotetrazolium blue, ferrocene and derivatives of the same, osmium complex, ruthenium complex, $NAD^+$, $NADP^+$, and pyrroloquinoline quinone (PQQ).

The reagent layers of the biosensor may further contain a hydrophilic polymer, a surfactant, and a saccharide. As these components further contained therein, those used in conventional biosensors of oxidase electrode types can be used.

In an exemplary embodiment, the biosensor used in the measurement method of the present invention is equipped with two or more independent electrode systems. Such a biosensor enables measurement wherein influences by dissolved oxygen are corrected, with only one measurement operation.

Therefore, the present invention in still another aspect relates to a biosensor used in the measurement method of the present invention, the biosensor comprising: two or more independent electrode systems each of which has a working electrode and a counter electrode provided on a substrate; and an oxidase, and a mediator as required, the oxidase and the mediator being provided on the two or more electrode systems. As described above, it is preferable that on the two or more independent electrode systems, reagent layers having different conditions are formed, respectively. More specifically, the reagent layers are preferably reagent layers that differ in at least one of a type and/or amount of an oxidase, a type and/or amount of a mediator, a type and/or amount of a hydrophilic polymer, a type and/or amount of a surfactant, a type and/or amount of a saccharide, and the like. Therefore, the present invention in still another aspect relates to a biosensor comprising: two or more independent electrode systems each of which has a working electrode and a counter electrode provided on a substrate; and oxidase-containing reagents provided respectively on the two or more electrode systems, the oxidase-containing reagents being capable of measuring a single target object in a single sample under different conditions.

An embodiment of a biosensor used in a measurement method according to the present invention is explained below with reference to FIG. 1. FIG. 1 is an exemplary schematic view illustrating a configuration of an embodiment of a biosensor according to the present invention. The biosensor of the present embodiment comprises: two independent electrode systems each of which has a working electrode 2 and a counter electrode 3 that are provided on a substrate 1; reagent layers 4 including an oxidase and a mediator, the reagent layers being provided on the electrode systems, respectively; a flow path 5; and air vents 6. The biosensor of the present invention, however, is not limited to this embodiment. In the biosensor shown in FIG. 1, a sample introduced into the flow path 5 flows toward the air vents 6, branches at a branching point, and is brought into contact with the two reagent layers 4 provided on the electrodes 2 and 3, where reaction occurs. The results of the reaction are detected from the electrodes 2 and 3.

[Measurement Device]

The present invention in still another aspect relates to a measurement device that comprises: a sensor section for obtaining information about measurement results of two or more types obtained from reactions between a target object in a sample and an oxidase under different conditions of two or more types; a memory section for storing a correction method; an arithmetic section for selecting the correction method stored in the memory section based on the information obtained by the sensor section, and calculating a corrected value of the information by the correction method; and a display section for displaying the corrected value. The measurement device of the present invention can be used in the measurement method of the present invention.

Figure 2:
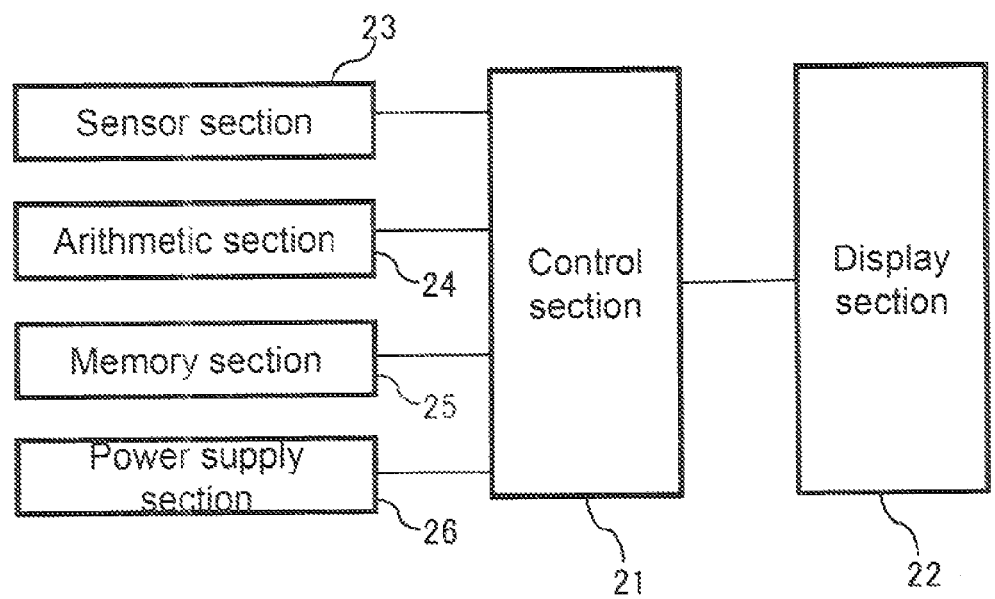
FIG. 2 is a block diagram illustrating a configuration of one embodiment of a measurement device according to the present invention.

An embodiment of a measurement device according to the present invention is explained below with reference to FIG. 2. FIG. 2 is an exemplary block diagram illustrating a configuration of an embodiment of a measurement device according to the present invention. In FIG. 1, the measurement device of the present embodiment includes a control section 21, a display section 22, a sensor section 23, an arithmetic section 24, a memory section 25, and a power source section 26. The measurement device of the present invention may have a configuration in which a part or all of these sections including the control section, the display section, the sensor section, the arithmetic section, and the memory section are integrally provided, or alternatively, may have a configuration in which they are individually provided.

The sensor section 23 is a section to which a biosensor is connectable and from which, after the biosensor is connected (attached), information, for example, electric current values, is obtained. Therefore, the sensor section may include a voltage application portion, an electric current value determination portion, and the like. The memory section 25 is intended, for example, to store a correction method, a correction coefficient, etc., and to store data and the like to be used in selection of a correction method.

The arithmetic section 24 is intended to set and/or select a correction method stored in the memory section 25 based on information obtained by the sensor section 23, and to calculate a corrected value of the information corrected by the correction method. The selection of a correction method can be performed by, for example, comparing information obtained by the sensor section 23 with the following data stored in the memory section 25: data that relate measurement values and dissolved oxygen concentrations with each other; and/or data that relate measurement values and contents of correction such as correction coefficients with each other. In the present invention, "information obtained by the sensor section 23" may include measurement values detected by the biosensor in the sensor section, and data based on the measurement values (for example, statistic values such as average values and dispersion, a difference between two measurement values, or the like). The calculation of the corrected value may be decided appropriately by the selected correction method, and may be carried out by, for example, multiplying a measurement value with a correction coefficient. Further, the arithmetic section 24 can calculate a concentration of a target object, and the like, using calibration curves and the like, in the case where the corrected value is an electric current value or the like.

The display section 22 is intended to display results of arithmetic operations by the arithmetic section 24, for example, corrected concentrations, etc., predicted values regarding dissolved oxygen in a sample, a correction coefficient, and the like. The display 22 is formed with, for example, a liquid crystal display device.

The power supply section 26 is intended to supply electric power to the control section 21, the display section 22, the sensor section 23, the arithmetic section 24, and the memory section 25. Further, in the case where the measurement device is a measurement device for a biosensor having electrodes, the power supply section 26 is used for applying a voltage across a working electrode and a counter electrode of the biosensor, and determining an amount of electrons transferred between the working electrode and the mediator. Further, the control section 21 is intended to control the display section 22, the sensor section 23, the arithmetic section 24, the memory section 25, and the power supply section 26.

Figure 3:
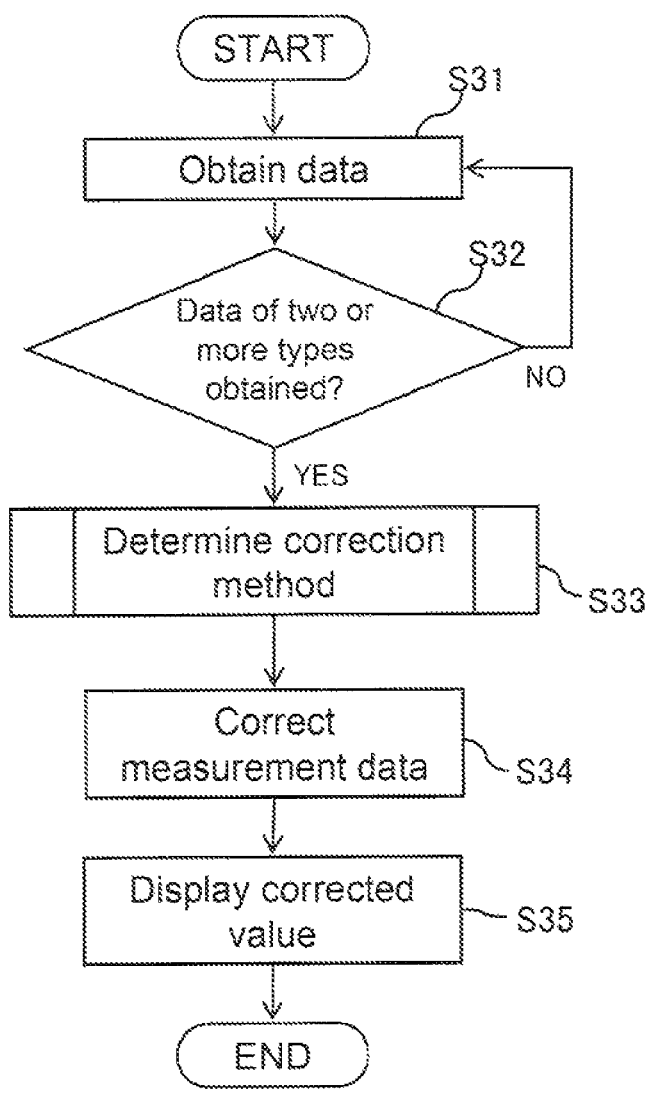
FIG. 3 is a flowchart showing an action of one embodiment of the measurement device according to the present invention.

Referring to the flowchart of FIG. 3, the following explains a method for measuring a target object with use of the measurement device shown in FIG. 2, taking as an example a case where the target object is glucose and the biosensor is a biosensor having electrode systems. Needless to say, however, the following explains merely one example, and the present invention is not limited to this.

First, a biosensor is attached to the sensor section 23 of the measurement device. Then, a sample such as blood is introduced into the biosensor, so as to react with a target object in the sample with an oxidase. Then, in the sensor section 23, a voltage is applied across a working electrode and a counter electrode of the biosensor, and a response current at that time is measured, whereby a measurement value (data) is obtained (S31). Whether or not measurement values (data) under different conditions of two or more types have been obtained is determined by the control section 21 (S32). In the case where the control section 21 determines that measurement values under different conditions of two or more types have not been obtained, the attempt of obtaining data is repeated again (S31). In the case where the control section 21 determines that measurement values under different conditions of two or more types have been obtained, the arithmetic section 24 performs a correction method determination operation (S33). In the correction method determination operation, the correction method is decided and set with reference to, for example, data thus obtained and a correction method preliminarily stored in the memory section 24. Then, data are corrected by the correction method thus set (S34), and a corrected value, or a concentration calculated based on the corrected value, etc., is displayed on the display section 22 (S35).

EXAMPLE

Measurement of Glucose by Two GOD Electrode System (A and B)

Using a biosensor provided with two GOD electrode systems (A and B), samples 1 to 3 were subjected to measurement operations. Reagents contained in reagent layers in the electrode systems A and B are as shown in Table 1 below. It should be noted that the unit (U) in Table 1 is defined to be an amount of enzyme that is capable of altering 1 micromole (μmol) of a substrate per one minute under optimal conditions (at a temperature of 30° C., and at a degree of acidity at which the chemical reaction proceeds most). Further, concentrations of glucose and dissolved oxygen in each sample are as shown in Table 2 below. Samples 1 to 3 are prepared using venous blood. The concentration of glucose was adjusted by adding glucose, and the concentration of dissolved oxygen was adjusted by shaking a tube containing the venous blood. It should be noted that the method for measuring the concentration of glucose and the concentration of dissolved oxygen is as follows.

TABLE 1

| | Component | | |
|---|---|---|---|
| Reagent layer of biosensor | Enzyme (GOD) | Mediator (Ruthenium complex) | Surfactant (Sucrose laurate) |
| System A | 2.0 U | 20 μg | 0.2 ng |
| System B | 0.5 U | 20 μg | 0.2 ng |

TABLE 2

| | Composition | |
|---|---|---|
| | Glucose | Dissolved oxygen |
| Sample 1 | 336 mg/dL | 30 mmHg |
| Sample 2 | 336 mg/dL | 70 mmHg |
| Sample 3 | 336 mg/dL | 110 mmHg |

[Measurement by Biosensor]

Using the biosensor provided with the above-described reagent layers (systems A and B), the samples 1 to 3 were measured (n=8). It should be noted that, regarding the measurement device, GA-1150 (trade name, produced by ARKRAY Inc.) was used as a glucose concentration meter, and ABL5 (trade name, produced by Radiometer) was used as a dissolved oxygen concentration meter. The results of the measurement are shown in Table 3 below.

TABLE 3

| | n | 1 | 2 | 3 | 4 | 5 | 6 | 7 | 8 |
|---|---|---|---|---|---|---|---|---|---|
| Sample 1 | System A | 11.23716 | 11.04659 | 11.65763 | 12.89393 | 10.70419 | 10.20777 | 10.82521 | 10.70419 |
| | System B | 10.69173 | 10.14014 | 10.34778 | 9.572999 | 10.59562 | 10.32179 | 9.706331 | 10.59562 |
| Sample 2 | System A | 10.44701 | 10.16902 | 9.675613 | 9.055767 | 10.94827 | 10.53663 | 9.667293 | 10.94827 |
| | System B | 9.952365 | 9.894451 | 9.670695 | 8.949746 | 9.817386 | 9.247258 | 9.84442 | 9.817386 |
| Sample 3 | System A | 9.311172 | 10.01974 | 10.06494 | 9.952288 | 9.470454 | 10.29546 | 9.837839 | 9.470454 |
| | System B | 9.378793 | 10.20714 | 10.6195 | 9.855481 | 10.06338 | 9.586116 | 10.76204 | 10.06338 |

Unit: μA

[Relating of Measurement Value and Dissolved Oxygen Concentration, and Decision of Correction Method]

Based on the data shown in Table 3 above, the measurement values of the systems A and B and concentrations of dissolved oxygen in the samples were related with one another, and a correction method as shown below was decided. It should be noted that in the present example, the correction coefficient mentioned below is 1.04.

Figure 4:
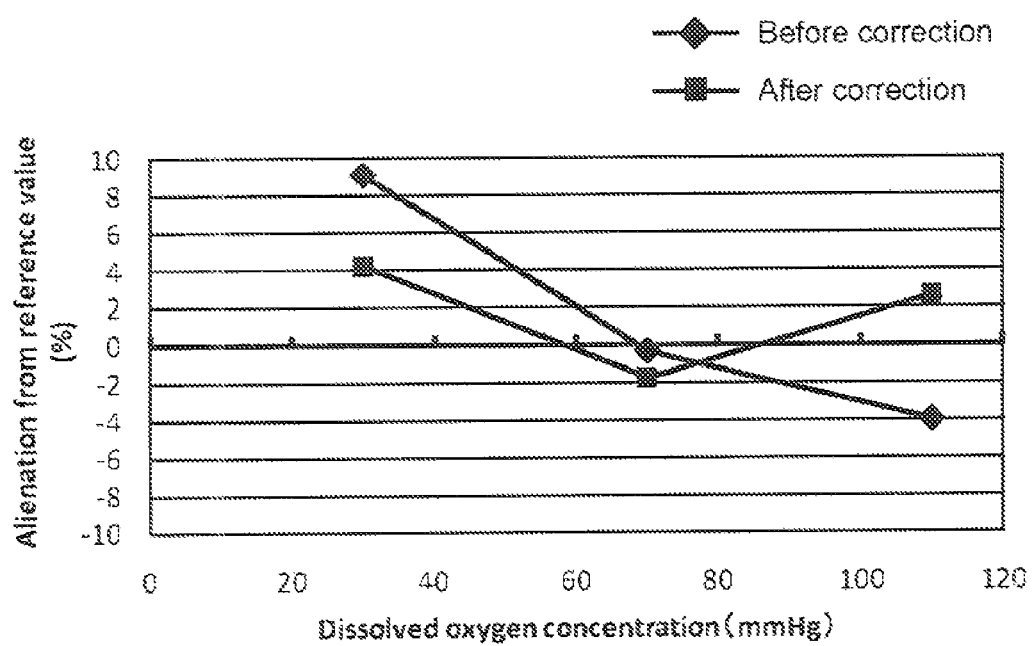
FIG. 4 is a graph showing results of examples.

Corrected value=(sample concentration determined from data of system $A$)×(measurement value of system $B$/measurement value of system $A$)×correction coefficient The results of correction by the above-described correction method are shown in Table 4 below and FIG. 4. The table 4 below shows average values of non-corrected values (concentrations obtained by referring to only measurement value of the system A and applying the same to a calibration curve), relative standard deviations (S.D.), coefficients of variation (C.V.), alienations (%) from a reference value (336 mg/dL), and corresponding values after correction. FIG. 4 is a graph showing the relationship between concentrations of dissolved oxygen in samples, and alienations (%) from the reference value before correction and those after the correction.

TABLE 4

|  | Non-corrected value (Data obtained from system A) | | | | Corrected value | | | |
| --- | --- | --- | --- | --- | --- | --- | --- | --- |
|  | Dissolved oxygen | Average (mg/dL) | S.D. (mg/dL) | C.V. | Alienation from reference value (%) | Average (mg/dL) | S.D. (mg/dL) | C.V. | Alienation from reference value (%) |
| Sample 1 | 30 mmHg | 366.63 | 26.51 | 7.2% | 9.12 | 350.13 | 14.43 | 4.1% | 4.21 |
| Sample 2 | 70 mmHg | 335.00 | 21.72 | 6.5% | −0.30 | 330.22 | 12.06 | 3.7% | −1.72 |
| Sample 3 | 110 mmHg | 322.77 | 11.23 | 3.5% | −3.94 | 344.74 | 16.10 | 4.7% | 2.60 |

As shown in Table 4 and FIG. 4, measurement values with the influence by dissolved oxygen being reduced were obtained by the above-described correction method.

INDUSTRIAL APPLICABILITY

The present invention is useful in the medical field, the life science field, and the biological research field.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for providing a corrected measurement of a target object in a sample, wherein the sample comprises dissolved oxygen, the method comprising:
    obtaining separate measurement values of the target object in the sample by reacting the target object with an oxidase under two or more different types of conditions; and
    performing a correction based on the measurement values obtained from the two or more different types of conditions to correct for the influence of the dissolved oxygen in the sample on the accuracy of the measurement value of the target object.

2. The method according to claim 1, wherein the reaction between the target object and the oxidase is performed in a biosensor that comprises
    two independent electrode systems, where each electrode system comprises a working electrode and a counter electrode, and
    a reagent layer comprising the oxidase provided on each of the two electrode systems.

3. The method according to claim 2, wherein the reagent layer further comprises a mediator.

4. The method according to claim 2, wherein the biosensor comprises more than two independent electrode systems.

5. The method according to claim 1, wherein the sample is selected from the group consisting of blood, plasma, serum and urine.

6. The method according to claim 5, wherein the sample is blood.

7. The method according to claim 1, wherein the target object is selected from the group consisting of glucose, lactic acid, bilirubin, cholesterol and ascorbic acid.

8. The method according to claim 7, wherein the target object is glucose.

9. The method according to claim 1, wherein the oxidase is selected from the group consisting of glucose oxidase, lactate oxidase, bilirubin oxidase, cholesterol oxidase, ascorbic acid oxidase, uric acid oxidase, peroxidase, sulfurous acid oxidase, amine oxidase, lysyl oxidase, lysine oxidase, amino acid oxidase, diamine oxidase, pyridoxine phosphate oxidase, protein-lysine 6-oxidase, acyl-CoA oxidase, alcohol oxidase, choline oxidase, pyruvic acid oxidase, sarcosine oxidase, tyramine oxidase and glycerophosphate oxidase.

10. The method according to claim 9, wherein the oxidase is glucose oxidase.

11. The method according to claim 1, wherein the mediator is selected from the group consisting of potassium ferricyanide, sodium ferricyanide, p-benzoquinone, phenazine methosulfate, indophenol, potassium β-naphthoquinone-4-sulfonate, 2,6-dichlorophenol indophenol, methylene blue, nitrotetrazolium blue, ferrocene, an osmium complex, a ruthenium complex, NAD$^+$, NADP$^+$ and pyrroloquinoline quinone (PQQ).

12. The method according to claim 11, wherein the mediator is a ruthenium complex.

13. The method according to claim 3, wherein the reagent layer further comprises at least one selected from the group consisting of a hydrophilic polymer, a surfactant and a saccharide.

* * * * *